United States Patent [19]

Hässig

[11] Patent Number: 4,692,524

[45] Date of Patent: Sep. 8, 1987

[54] PROCESS FOR THE PREPARATION OF PYRIMIDINE DERIVATIVES

[75] Inventor: Robert Hässig, Sisseln, Switzerland

[73] Assignee: Ciba-Geigy Corporation, Ardsley, N.Y.

[21] Appl. No.: 858,636

[22] Filed: May 2, 1986

[51] Int. Cl.[4] .................. C07D 239/60; C07D 239/56
[52] U.S. Cl. ..................................... 544/303; 544/313
[58] Field of Search ............................... 544/313, 303

[56] References Cited

U.S. PATENT DOCUMENTS 4,478,635 10/1984 Meyer et al. ............................ 71/92
4,545,811 10/1985 Meyer et al. ............................ 71/93

FOREIGN PATENT DOCUMENTS 0072347 2/1983 European Pat. Off. .
0084020 7/1983 European Pat. Off. .
0094790 11/1983 European Pat. Off. .

Primary Examiner—John M. Ford
Attorney, Agent, or Firm—Edward McC. Roberts; Kevin T. Mansfield

[57] ABSTRACT

The present invention relates to a process for the preparation of 2-mercapto-4,6-bis-fluoroalkoxypyrimidines of the formula

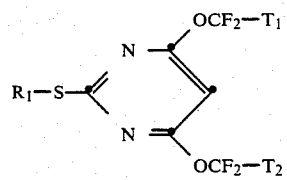

wherein $R_1$ is $C_1$-$C_4$alkyl, phenyl or benzyl and each of $T_1$ and $T_2$ independently of the other is hydrogen or a —$CHX_1X_2$ group, wherein each of $X_1$ and $X_2$ independently of the other is trifluoromethyl, fluorine, chlorine or bromine.

In accordance with this process, 2-mercapto-4-halo-6-hydroxy-pyrimidines of the formula

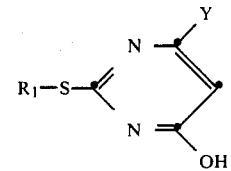

wherein $R_1$ is as defined above and Y is chlorine or bromine, are reacted with chlorodifluoromethane or a 1,1-difluoroalkene of the formula

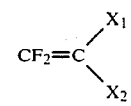

wherein each of the $X_1$ and $X_2$ independently of the other is trifluoromethyl, fluorine, chlorine or bromine, in an inert solvent and in the presence of a strong base, to give a 2-mercapto-4-halo-6-fluoro-alkoxypyrimidine of the formula

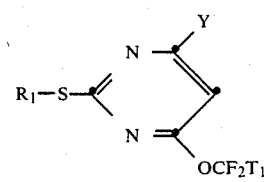

wherein $R_1$, Y and $T_1$ are as defined above, said 2-mercapto-4-halo-6-fluoroalkoxypyrimidine is converted by subsequent reaction with an alkali metal nitrite or an alkaline earth metal nitrite into a 2-mercapto-4-hydroxy-6-fluoroalkoxypyrimidine of the formula

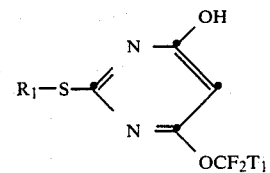

wherein $R_1$ and $T_1$ are as defined above, and then said 2-mercapto-4-hydroxy-6-fluoroalkoxypyrimidine is converted by reaction with chlorodifluoromethane or a 1,1-difluoroalkene of the above formula into a 2-mercapto-4,6-bix-fluoroalkoxypyrimidine of the above formula.

The 2-mercapto-4,6-bis-fluoroalkoxypyrimidines of the above formula are intermediates for the preparation of herbicidally effective sulfonylureas.

23 Claims, No Drawings

PROCESS FOR THE PREPARATION OF PYRIMIDINE DERIVATIVES

The present invention relates to a process for the preparation of 2-mercapto-4,6-bis-fluoroalkoxypyrimidines of formula I

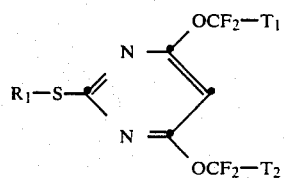

wherein $R_1$ is $C_1$–$C_4$alkyl, phenyl or benzyl and each of $T_1$ and $T_2$ independently of the other is hydrogen or a —$CHX_1X_2$ group, wherein each of $X_1$ and $X_2$ independently of the other is trifluoromethyl, fluorine, chlorine or bromine.

The 2-mercapto-4,6-bis-fluoroalkoxypyrimidines of formula I are valuable intermediates. They can for example be converted by oxidation into the corresponding sulfones, which on subsequent reaction with ammonia or a primary amine yield the corresponding 2-amino-4,6-bis-fluoroalkoxypyrimidines, which on subsequent reaction with a suitable phenylsulfonylisocyanate or N-(phenylsulfonyl)carbamate afford herbicidally effective sulfonylureas. Such herbicidally effective sulfonylureas are described for example in published European patent applications Nos. 0 072 347, 0 084 020 and 0 094 790.

The 2-mercapto-4,6-bis-fluoroalkoxypyrimidines of formula I can in principle be prepared by reacting 2-mercapto-4,6-dihydroxypyrimidines direct with chlorodifluoromethane or a corresponding 1,1-difluoroalkene. However, the 2-mercapto-4,6-bis-fluoroalkoxypyrimidines of formula I are obtained by this process only in unsatisfactory yield. For example, by reacting 4,6-dihydroxy-2-methylthiopyrimidine with chlorodifluoromethane, in a reaction medium consisting of dioxane and an aqueous sodium hydroxide solution, 4,6-bis-difluoromethoxy-2-methylthiopyrimidine is obtained merely in a yield of 25% of theory (qv. U.S. Pat. No. 4,542,216, Example 5).

Accordingly, it is the object of the present invention to provide a process for the preparation of the 2-mercapto-4,6-bis-fluoroalkoxypyrimidines of formula I, by which process said compounds can be prepared in good yield.

In accordance with the present invention, it is proposed to prepare the 2-mercapto-4,6-bis-fluoroalkoxypyrimidines of formula I by reacting a 2-mercapto-4-halo-6-hydroxypyrimidine of formula II

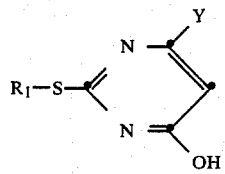

wherein $R_1$ is as defined for formula I and Y is chlorine or bromine, with chlorodifluoromethane or a 1,1-difluoroalkene of formula III

wherein each of $X_1$ and $X_2$ independently of the other is trifluoromethyl, fluorine, chlorine or bromine, in an inert solvent and in the presence of a strong base, to give a 2-mercapto-4-halo-6-fluoroalkoxypyrimidine of formula IV

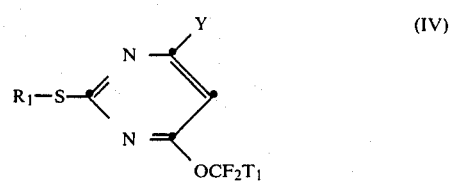

wherein $R_1$, Y and $T_1$ are defined above, converting said 2-mercapto-4-halo-6-fluoroalkoxypyrimidine of formula IV by subsequent reaction with an alkali metal nitrite or an alkaline earth metal nitrite, in a polar solvent, into a 2-mercapto-4-hydroxy-6-fluoroalkoxypyrimidine of formula V

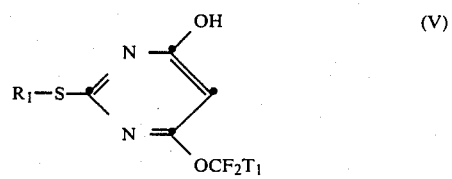

wherein $R_1$ and $T_1$ are as defined above, and then converting said 2-mercapto-4-hydroxy-6-fluoroalkoxypyrimidine of formula V by reaction with chlorodifluoromethane or a 1,1-difluoroalkene of formula III, in an inert solvent and in the presence of a strong base, into a 2-mercapto-4,6-bis-fluoroalkoxypyrimidine of formula I.

Preferred 2-mercapto-4,6-bis-fluoroalkoxypyrimidines of formula I which can be prepared by the process of this invention are those wherein $R_1$ is $C_1$–$C_2$alkyl or benzyl, $T_1$ is hydrogen and $T_2$ is a —$CHFX_1$ group. Particularly preferred 2-mercapto-4,6-bis-fluoroalkoxypyrimidines of formula I are those wherein $R_1$ is $C_1$–$C_2$alkyl and $T_1$ and $T_2$ are hydrogen.

The 2-mercapto-4-halo-6-hydroxypyrimidines of formula II are known compounds which can be prepared in good yield in known manner by reacting 2-mercapto-4,6-dihydroxypyrimidines with an inorganic acid halide, such as thionyl chloride, phosgene, phosphorus oxychloride or phosphorus pentachloride, to give the corresponding 2-mercapto-4,6-dihalopyrimdines, and effecting subsequent partial hydrolysis.

The reaction of the 2-mercapto-4-halo-6-hydroxypyrimidines of formula II with chlorodifluoromethane or a 1,1-difluoroalkene of formula III is advantageously carried out in an inert solvent. Particularly suitable solvents are polar solvents such as liquid alkanecarboxamides, nitriles, dialkyl sulfoxides, ethers, ketones and alcohols. Tertiary amines may also be used as solvents. Specifically, examples of suitable solvents are formamide, N,N-dimethylformamide, N,N-dimethylacetamide, acetonitrile, dimethyl sulfoxide, diethyl ether, tetrahydrofuran, dioxane, acetone, methy ethyl ketone, methyl isobutyl ketone, and $C_1$–$C_4$alkanols such as methanol, ethanol and isopropanol. Suitable tertiary amines are in particular triethylamine, pyridine, picolines, or N,N-dialkylanilines, in particular N,N-dimethylaniline. Dioxane is a preferred solvent.

Suitable strong bases, in the presence of which the reaction of a 2-mercapto-4-halo-6-hydroxypyrimidine of formula II with chlorodifluoromethane or a 1,1-difluoroalkene of formula III is carried out, are alkali metal hydroxides, alkaline earth metal hydroxides and tertiary organic bases. Examples of suitable bases are lithium hydroxide, sodium hydroxide, potassium hydroxide, calcium hydroxide, strontium hydroxide, barium hydroxide, triethylamine, N,N-dimethylaniline and pyridine. Preferred bases are sodium hydroxide, potassium hydroxide and calcium hydroxide, with sodium hydroxide and potassium hydroxide being particularly preferred. The bases are employed in an at least stoichiometric amount. However, the bases are usually employed in excess. For example, the use of 5 to 10 equivalents of base per mole of 2-mercapto-4-halo-6-hydroxypyrimidine of formula II has proven successful in practice. The bases can advantageously be employed in the form of their aqueous solutions, e.g. in the form of a 50% sodium hydroxide solution or of a 50% potassium hydroxide solution.

The reaction of a 2-mercapto-4-halo-6-hydroxypyrimidine of formula II with chlorodifluoromethane or a 1,1-difluoro-2,2-haloethylene of formula III is advantageously carried out in the presence of a phase transfer catalyst. Suitable phase transfer catalysts are in particular crown ethers and quaternary ammonium salts. Examples of particularly suitable phase transfer catalysts are 18-crown-6, tetrabutylammonium bromide and benzyltriethylammonium chloride. The phase transfer catalysts are usually employed in an amount of 1 to 20 mol%, based on the 2-mercapto-4-halo-6-hydroxypyrimidine of formula II. It is preferred to employ 2.5 to 5 mol% of phase transfer catalyst per mole of 2-mercapto-4-halo-6-hydroxypyrimidine of formula II.

The pressure under which the reaction of a 2-mercapto-4-halo-6-hydroxypyrimidine of formula II with chlorodifluoromethane or a 1,1-difluoroalkene of formula III is carried out may vary within wide limits. Suitable pressures are in the range from 0.1 to 20 bar. It is preferred to carry out the reaction under normal pressure or under a moderately increased pressure. A preferred pressure range in which the reaction can be carried out is from 0.8 to 5 bar.

Suitable polar solvents, in the presence of which the reaction of a 2-mercapto-4-halo-6-fluoroalkoxypyrimidine of formula IV with an alkali metal nitrite or an alkaline earth metal nitrite is carried out, are liquid alkanecarboxamides and alkanecarboxylic acid nitriles, lactams, dialkyl sulfoxides and $C_1$–$C_4$alkanols. Specifically, examples of suitable solvents are formamide, N,N-dimethylformamide, N,N-dimethylacetamide, N-methylpyrrolidone, dimethyl sulfoxide, methanol, ethanol and isopropanol. Preferred solvents, in the presence of which the reaction of a 2-mercapto-4-halo-6-fluoroalkoxypyrimidine of formula IV with an alkali metal nitrite or an alkaline earth metal nitrite can be carried out, are formamide, N,N-dimethylformamide and dimethyl sulfoxide. N,N-dimethylformamide is a particularly preferred solvent.

Examples of suitable alkali metal nitrites and alkaline earth metal nitrites are sodium nitrite, potassium nitrite, ammonium nitrite, magnesium nitrite, calcium nitrite and barium nitrite. Preferred nitrites are sodium nitrite and potassium nitrite. The nitrites are employed in an at least stoichiometric amount, based on the 2-mercapto-4-halo-6-fluoroalkoxypyrimidine of formula IV. However, an excess of 2 to 5 moles of nitrite per mole of 2-mercapto-4-halo-6-fluoroalkoxypyrimidine of formula IV is usually employed. It is preferred to employ 2 to 4 moles of nitrite per mole of 2-mercapto-4-halo-6-fluoroalkoxypyrimidine of formula IV.

The reaction of a 2-mercapto-4-halo-6-fluoroalkoxypyrimidine of formula IV with an alkali metal nitrite or an alkaline earth metal nitrite is advantageously carried out at elevated temperature. Suitable reaction temperatures are in the range from 50° to 200° C. The reaction is preferably carried out at a temperature in the range from 130° to 160° C.

The reaction of a 2-mercapto-4-hydroxy-6-fluoroalkoxypyrimidine of formula V with chlorodifluoromethane or a 1,1-difluoroalkene of formula III corresponds substantially to the above-described reaction of a 2-mercapto-4-halo-6-hydroxypyrimidine of formula II with chlorodifluoromethane or a 1,1-difluoro-2,2-dihaloethylene of formula III. Accordingly, the statements made in connection with the reaction of the 2-mercapto-4-halo-6-hydroxypyrimidine of formula II with chlorodifluoromethane or a 1,1-difluoroalkene of formula III concerning suitable solvents, reaction temperatures and catalysts apply in analogous manner to this reaction.

The 2-mercapto-4-halo-6-fluoroalkoxypyrimidines of formula IV, which can be obtained by reacting a 2-mercapto-4-halo-6-hydroxypyrimidine of formula II with chlorodifluoromethane or a 1,1-difluoroalkene of formula III, and the 2-mercapto-4-hydroxy-6-fluoroalkoxypyrimidines of formula V, which can be prepared by subsequently reacting said 2-mercapto-4-halo-6-fluoroalkoxypyrimidines of formula IV with an alkali metal nitrite or an alkaline earth metal nitrite, are novel compounds and likewise constitute an object of the present invention.

The process of the present invention makes it possible to prepare the 2-mercapto-4,6-bis-fluoroalkoxypyrimidines of formula I in yields of more than 50% of theory by starting from the readily accessible 2-mercapto-4-halo-6-hydroxypyrimidines of formula II. Since the 2-mercapto-4-halo-6-hydroxypyrimidines of formula II employed as starting materials can in turn be prepared in yields of more than 80% of theory by starting from the corresponding 2-mercapto-4,6-dihydroxypyrimidines, the yield of 2-mercapto-4,6-bis-fluoroalkoxypyrimidines of formula I which can be obtained by the process of the present invention is more than 40% of theory, based on the corresponding 4,6-dihydroxypyrimidines, whereas, as mentioned at the outset, the direct reaction of 4,6-dihydroxypyrimidines with chlorodifluoromethane affords the 4,6-bis-difluoromethoxy compounds merely in a yield of 25% of theory.

The process of the present invention is illustrated in more detail by the following Examples.

EXAMPLE 1

Preparation of 4-chloro-6-difluoromethoxy-2-methylthiopyrimidine 6.8 g (0.036 mole) of 4-chloro-6-hydroxy-2-methylthiopyrimidine are suspended in 25 ml 50% potassium hydroxide solution, 25 ml of water and 100 ml of dioxane. After the addition of 0.5 g of 18-crown-6, the reaction mixture is heated to 40° C., and 10 g of chlorodifluoromethane are subsequently introduced over 3 hours. The mixture is then cooled to room temperature, the phases are separated and the organic phase is evaporated to dryness. The residue is crystallised from methanol/water, affording 6.9 g (84.4% of theory) of 4-chloro-6-difluoromethoxy-2-methylthiopyrimidine with a melting point of 36°–37° C. The substance has a boiling point of 76°–78° C. at 0.15 mbar.

EXAMPLE 2

Preparation of 4-difluoromethoxy-6-hydroxy-2-methylthio-1,3-pyrimidine

Over 50 minutes, a solution of 8.8 g (0.127 mole) of sodium nitrite in 10 ml of dimethylformamide is added dropwise at 140° C. to a solution of 8.7 g (0.038 mole) of 4-chloro-6-difluoromethoxy-2-methylthiopyrimidine in 10 ml of dimethylformamide. When the addition of the sodium nitrite is complete, the mixture is stirred for 2 hours at 140° to 150° C. The solvent is then evaporated off in vacuo and the residue is crystallised from 1N hydrochloric acid, affording 5.6 g (70% of theory) of 4-difluoromethoxy-6-hydroxy-2-methylthiopyrimidine with a melting point of 236°–237° C.

EXAMPLE 3

Preparation of 4,6-bis-difluoromethoxy-2-methylthiopyrimidine 14.0 g (0.067 mole) of 4-difluoromethoxy-6-hydroxy-2-methylthiopyrimidine are suspended in 18 ml of 50% potassium hydroxide solution, 10 ml of water and 160 ml of dioxane. After the addition of 0.5 g of 18-crown-6, the reaction mixture is heated to 40° C., and 20 g of chlorodifluoromethane are subsequently introduced over 5 hours. The aqueous phase is then separated and the organic phase is distilled under a high vacuum, affording 15.0 g (86.4% of theory) of 4,6-bis-difluoromethoxy-2-methylthiopyrimidine with a boiling point of 63° C./0.06 mbar. The substance melts at 46°–48° C.

EXAMPLE 4

Preparation of 4-difluoromethoxy-6-(1,1,2,3,3,3-hexafluoropropoxy)-2-methylthiopyrimidine With stirring, 21.0 g (0.14 mole) of hexafluoropropylene are introduced over 6 hours at 20°–25° C. into a solution of 20.8 g (0.1 mole) of 4-difluoromethoxy-6-hydroxy-2-methylthiopyrimidine and 1.0 g of triethylamine in 80 ml of dimethylformamide. When the addition of the hexafluoropropylene is complete, the reaction mixture is stirred for a further 30 minutes and then filtered through Hyflo. The clear filtrate is freed from the solvent at a bath temperature of 70° C. and at a pressure of 33 mbar. 31.2 g (87% of theory) of crude product are obtained as residue. The crude product is purified by distillation under a high vacuum. Yield: 25.2 g (70.4% of theory); boiling point: 88° C./0.33 mbar.

The following 2-mercapto-4,6-bis-fluoroalkoxypyrimidines of formula I are obtained by procedures analogous to those described in Examples 1 to 3.

| $R_1$ | $T_1$ | $T_2$ | |
|---|---|---|---|
| $CH_3$ | H | CHClF | b.p.: 117° C./0.07 mbar |
| $C_2H_5$ | H | H | b.p.: 85° C./0.05 mbar |
| 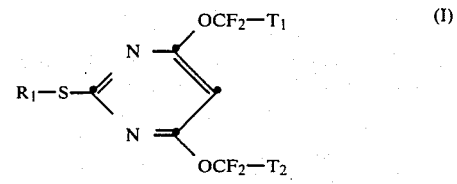 | H | H | m.p.: 40–43° C. |
| $C_2H_5$ | H | CHClF | |

What is claimed is:

1. A process for the preparation of a 2-mercapto-4,6-bis-fluoroalkoxypyrimidine of formula I

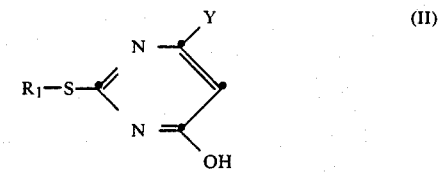

wherein $R_1$ is $C_1$–$C_4$alkyl, phenyl or benzyl and each of $T_1$ and $T_2$ independently of the other is hydrogen or a $-CHX_1X_2$ group, wherein each of $X_1$ and $X_2$ independently of the other is trifluoromethyl, fluorine, chlorine or bromine, which process comprises reacting a 2-mercapto-4-halo-6-hydroxypyrimidine of formula II

wherein $R_1$ is as defined for formula I and Y is chlorine or bromine, with chlorodifluoromethane or a 1,1-difluoroalkene of formula III $$CF_2=C\begin{matrix}X_1\\X_2\end{matrix} \quad (III)$$

wherein each of $X_1$ and $X_2$ independently of the other is trifluoromethyl, fluorine, chlorine or bromine, in an inert solvent and in the presence of a strong base, to give a 2-mercapto-4-halo-6-fluoroalkoxypyrimidine of formula IV

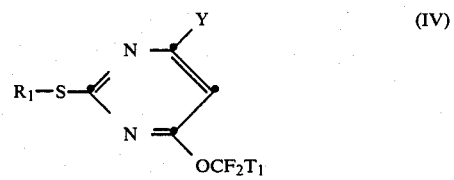

wherein $R_1$, Y and $T_1$ are as defined above, converting said 2-mercapto-4-halo-6-fluoroalkoxypyrimidine of formula IV by subsequent reaction with an alkali metal nitrite or an alkaline earth metal nitrite, in a polar solvent, into a 2-mercapto-4-hydroxy-6-fluoroalkoxypyrimidine of formula V

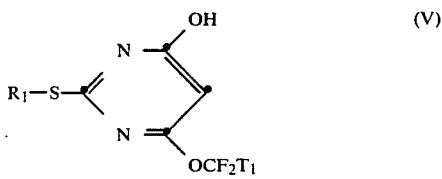

wherein $R_1$ and $T_1$ are as defined above, and then converting said 2-mercapto-4-hydroxy-6-fluoroalkoxypyrimidine of formula V by reaction with chlorodifluoromethane or a 1,1-difluoroalkene of formula III, in an inert solvent and in the presence of a strong base, into a 2-mercapto-4,6-bis-fluoroalkoxypyrimidine of formula I.

2. A process according to claim 1, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in a liquid alkanecarboxamide, an alkanecarboxylic acid nitrile, a dialkyl sulfoxide, an ether, a ketone or an alcohol as solvent.

3. A process according to claim 2, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in formamide, N,N-dimethylformamide, N,N-dimethylacetamide, acetonitrile, dimethyl sulfoxide, diethyl ether, tetrahydrofuran, dioxane, acetone, methyl ethyl ketone, methyl isobutyl ketone or a $C_1$–$C_4$alkanol as solvent.

4. A process according to claim 2, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in dioxane as solvent.

5. A process according to claim 1, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in the presence of an alkali metal hydroxide or an alkaline earth metal hydroxide.

6. A process according to claim 5, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in the presence of lithium hydroxide, sodium hydroxide, potassium hydroxide, calcium hydroxide, strontium hydroxide or barium hydroxide.

7. A process according to claim 6, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in the presence of sodium hydroxide or potassium hydroxide.

8. A process according to claim 1, wherein the bases are employed in the form of their aqueous solutions.

9. A process according to claim 1, wherein the reaction of a 2-mercapto-4-halo-6-hydroxypyrimidine of formula II or of a 2-mercapto-4-hydroxy-6-fluoroalkoxypyrimidine of formula V with chlorodifluoromethane or a 1,1-difluoroalkene of formula III is carried out in the presence of a phase transfer catalyst.

10. A process according to claim 9, wherein the phase transfer catalyst is employed in an amount of 1 to 20 mol%, based on the 2-mercapto-4-halo-6-hydroxypyrimidine of formula II or the 2-mercapto-4-hydroxy-6-fluoroalkoxypyrimidine of formula V.

11. A process according to either of claims 9 or 10, wherein a crown ether or a quaternary ammonium salt is used as phase transfer catalyst.

12. A process according to either of claims 9 or 10, wherein 18-crown-6, tetrabutylammonium bromide or benzyltriethylammonium chloride is used as phase transfer catalyst.

13. A process according to claim 1, wherein the reaction of a 2-mercapto-4-halo-6-fluoroalkoxypyrimidine of formula IV with an alkali metal nitrite or an alkaline earth metal nitrite is carried out in a liquid alkanecarboxamide, a liquid alkanecarboxylic acid nitrile, a lactam, a dialkyl sulfoxide or a $C_1$–$C_4$alkanol.

14. A process according to claim 13, wherein the reaction of a 2-mercapto-4-halo-6-fluoroalkoxypyrimidine of formula IV with an alkali metal nitrite or an alkaline earth metal nitrite is carried out in formamide, N,N-dimethylformamide, N,N-dimethylacetamide, N-methylpyrrolidone, dimethyl sulfoxide, methanol, ethanol or isopropanol as solvent.

15. A process according to claim 14, wherein the reaction of a 2-mercapto-4-halo-6-fluoroalkoxypyrimidine of formula IV with an alkali metal nitrite or an alkaline earth metal nitrite is carried out in formamide, N,N-dimethylformamide or dimethyl sulfoxide as solvent.

16. A process according to claim 15, wherein the reaction of a 2-mercapto-4-halo-6-fluoroalkoxypyrimidine of formula IV with an alkali metal nitrite or an alkaline earth metal nitrite is carried out in N,N-dimethylformamide as solvent.

17. A process according to claim 1, wherein sodium nitrite, potassium nitrite, ammonium nitrite, magnesium nitrite, calcium nitrite or barium nitrite is used as alkali metal nitrite or alkaline earth metal nitrite.

18. A process according to claim 17, which comprises the use of sodium nitrite or potassium nitrite.

19. A process according to claim 1, wherein 2 to 4 moles of alkali metal nitrite or alkaline earth metal nitrite are used per mole of 2-mercapto-4-halo-6-fluoroalkoxypyrimidine of formula IV.

20. A process according to claim 1, wherein the reaction of a 2-mercapto-4-halo-6-fluoroalkoxypyrimidine of formula IV with an alkali metal nitrite or an alkaline earth metal nitrite is carried out at a temperature in the range from 50° to 200° C.

21. A process according to claim 20, wherein the reaction of a 2-mercapto-4-halo-6-fluoroalkoxypyrimidine of formula IV with an alkali metal nitrite or an alkaline earth metal nitrite is carried out at a temperature in the range from 130° to 160° C.

22. A 2-mercapto-4-halo-6-fluoroalkoxypyrimidine of formula IV

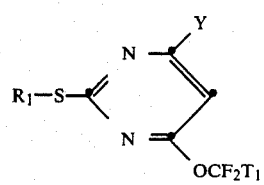

(IV)

wherein $R_1$ is $C_1$-$C_4$alkyl, phenyl or benzyl, Y is chlorine or bromine and $T_1$ is hydrogen or a —$CHX_1X_2$ group, wherein each of $X_1$ and $X_2$ independently of the other is trifluoromethyl, fluorine, chlorine or bromine.

23. A 2-mercapto-4-hydroxy-6-fluoroalkoxypyrimidine of formula V

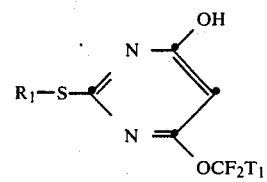

(V)

wherein $R_1$ is $C_1$-$C_4$alkyl, phenyl or benzyl and $T_1$ is hydrogen or a —$CHX_1X_2$ group, wherein each of $X_1$ and $X_2$ independently of the other is trifluoromethyl, fluorine, chlorine or bromine.

* * * * *